United States Patent [19]

Gonzales-Prevatt et al.

[11] Patent Number: 5,093,236
[45] Date of Patent: Mar. 3, 1992

[54] MICROBIOLOGICAL OIL PROSPECTING

[75] Inventors: Victoria Gonzales-Prevatt, Bartlesville, Okla.; Douglas M. Munnecke, Montara, Calif.

[73] Assignees: Genecor International, Inc., South San Francisco, Calif.; Geo-Microbial Technologies, Inc., Ochelata, Okla.

[21] Appl. No.: 541,469

[22] Filed: Jun. 22, 1990

Related U.S. Application Data

[63] Continuation of Ser. No. 244,415, Sep. 14, 1989, abandoned.

[51] Int. Cl.⁵ .............................................. C12Q 1/64
[52] U.S. Cl. ........................................ 435/9; 435/25; 435/810
[58] Field of Search .............................................. 435/9

[56] References Cited

U.S. PATENT DOCUMENTS

| | | |
|---|---|---|
| 2,234,637 | 3/1941 | Taggart . |
| 2,269,889 | 1/1942 | Blau . |
| 2,294,425 | 9/1942 | Sanderson . |
| 2,349,472 | 5/1944 | Taggart . |
| 2,665,237 | 1/1954 | Strawinski . |
| 2,777,799 | 1/1957 | Davis . |
| 2,861,921 | 11/1958 | Updegraff et al. . |
| 2,880,142 | 12/1956 | Hitzman ................................. 435/9 |
| 3,033,761 | 5/1962 | Brown . |
| 3,096,254 | 7/1963 | Hitzman . |
| 3,206,317 | 9/1965 | Golber . |
| 3,281,333 | 10/1966 | Hitzman . |
| 3,418,212 | 12/1968 | Fitzgibbons . |
| 4,026,767 | 5/1977 | Shih . |
| 4,728,608 | 3/1988 | Roberts et al. ........................ 435/810 |

FOREIGN PATENT DOCUMENTS

| | | |
|---|---|---|
| 55-397763 | 3/1980 | Japan . |
| 2147415 | 5/1985 | United Kingdom . |

OTHER PUBLICATIONS

Hitzman, Developments in Industrial Microbiology, vol. 2, "Comparison of Geomicrobiological Prospecting Methods Used by Various Investigators", Plenum Press, N.Y.

Primary Examiner—Sam Rosen
Attorney, Agent, or Firm—Burns, Doane, Swecker and Mathis

[57] ABSTRACT

This invention provides methods and systems for prospecting for subterranean oil and gas deposits by detecting the presence of hydrocarbon-consuming microorganisms in soil samples taken from a field of interest for production. A preferred method of this invention comprises suspending and diluting each soil sample in mineral salt solution, combining the sample with a selective growth, substrate such as an alcohol or aldehyde, and an oxidation-reduction dye in a gas-tight tube, incubating the sample and measuring the color change of the dye. Advantages of this system include: results obtained in short times (24 to 72 hours), substantially eliminates false positives, accurate results particularly when a spectrophotometer is used to measure the color changes, and it is automatable with computer controlled systems for processing samples, reading the color changes and calculating and plotting test results.

17 Claims, 8 Drawing Sheets

SURVEY #53

SURVEY #79

SURVEY #79, MOVING AVERAGE PLOT
EXAMPLE III

SURVEY # 93

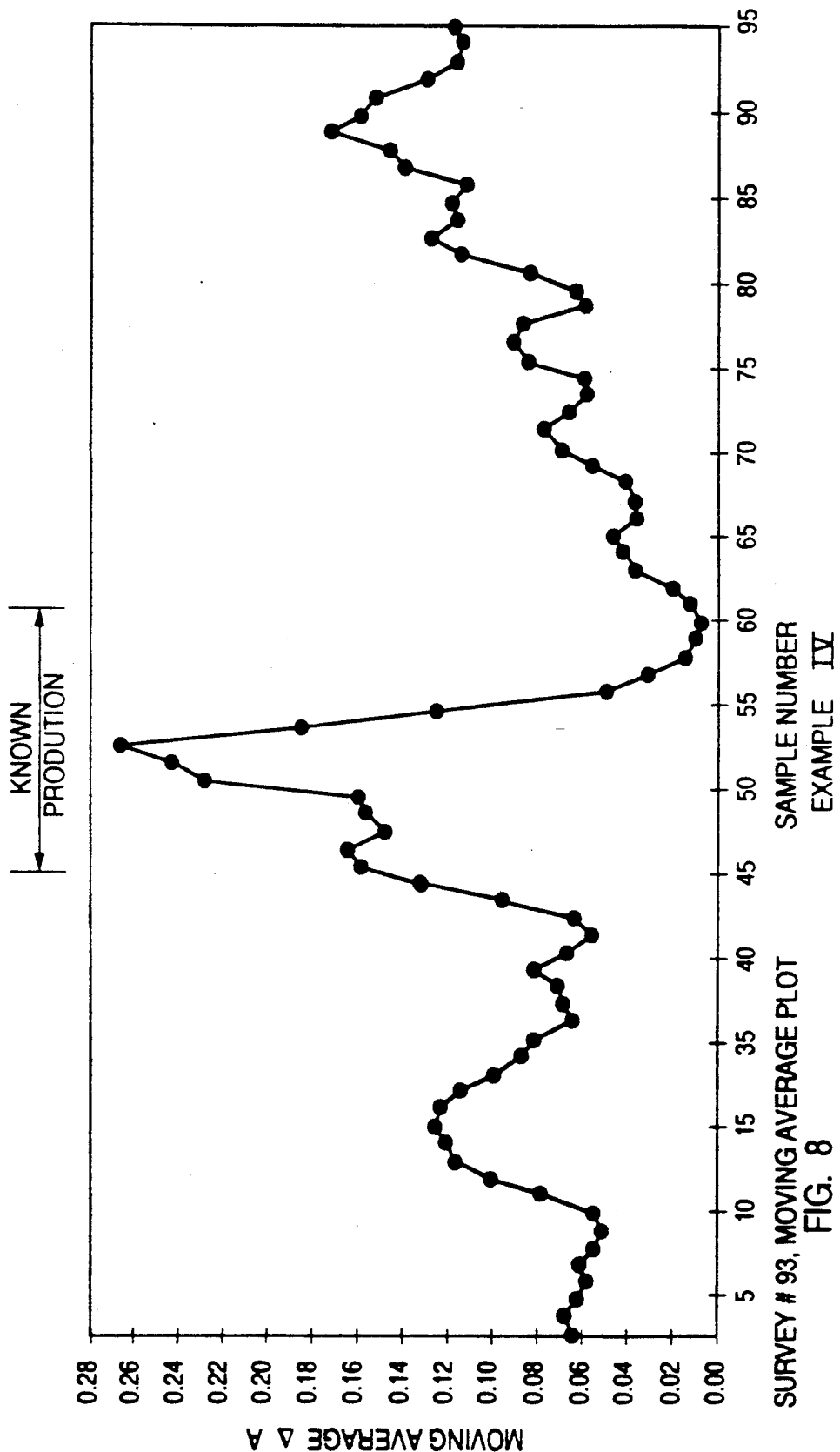

MICROBIOLOGICAL OIL PROSPECTING

This application is a continuation of application Ser. No. 07/244,415, filed 9/14/88, now abandoned.

FIELD OF THE INVENTION

The present invention relates to prospecting for subterranean oil and gas deposits and, more particularly, to the detection in a soil sample of hydrocarbon-consuming microorganisms indicative of the presence of oil or gas beneath the soil.

BACKGROUND OF THE INVENTION

Microbiological prospecting for petroleum is based on the theory that various hydrocarbons migrate from subterranean deposits to the surface of the earth. Such hydrocarbons are usually gases and have a marked effect on the surface of the soil. More specifically, it has been established with a considerable degree of certainty that these hydrocarbon gases feed certain microorganisms in the soil. Thus, the existence of a petroleum deposit can be recognized by either a high content of such microorganisms in the soil or by the presence in the soil of products resulting from the feeding of said microorganisms upon the hydrocarbon content of the soil. Three primary techniques have been employed: (1) gas utilization, which is the indirect measurement of the presence of hydrocarbon-consuming microorganisms by measuring the amount of a hydrocarbon consumed by such microorganisms; (2) direct measurement of the population of hydrocarbon-consuming microorganisms, e.g., by using plate counts; and (3) measurement of the metabolic products of hydrocarbon-consuming microorganisms.

The first of the above described techniques namely, gas utilization, typically involves isolating the hydrocarbon-consuming microorganisms from a soil sample and growing such microorganisms in the presence of hydrocarbon gases. By growing microorganisms isolated from soil samples in the presence of hydrocarbon gases, the type, amount and character of the resulting microbial growth are observed. This technique typically requires two weeks for its implementation and is somewhat unreliable since it wa based on subjective determinations of turbidity based on a five-point scale.

Variations of the gas-utilization technique have been made. U.S. Pat. No. 2,349,472 to Taggart describes a process wherein a soil sample is placed in a sealed chamber and the chamber filled with air and hydrocarbons. The drop in the pressure over a selected period of time indicates the bacterial content of the soil sample. Another gas utilization technique wherein pressure drops are measured is described in U.S. Pat. No. 2,665,237 to Strawinski, wherein a large excess of nutrient is used so as to ensure maximization of bacterial growth uniformly among the various samples and to render the contents of moisture and nutrient present in the sample itself inconsequential terms of the calculations carried out. The disclosures of these patents are incorporated herein by reference.

Several disadvantages have been found to exist with the gas-utilization techniques described above. A primary disadvantage is that the methods generally require several days to several weeks for completion of the tests before meaningful data or indications can be obtained. Another disadvantage is that the additional calculations based on hydrocarbon consumption by microorganisms contained in a soil sample can be very unreliable due to the highly adaptive nature of many microorganisms. It is known, for example, that microorganisms with the ability to grow on hydrocarbons are ubiquitous in nature. Therefore, although such microorganisms have the capability of utilizing hydrocarbons (or can be induced to utilize hydrocarbons upon their exposure to such compounds in the absence of their usual growth substrates), they can also metabolize organic compounds normally present in soil and not attributable to the presence of petroleum. Accordingly, measurement of the amounts of hydrocarbon-consuming microorganisms via gas consumption calculations does not necessarily mean that hydrocarbons derived from petroleum were present in the sample.

To overcome those disadvantages, it was proposed by Hitzman in U.S. Pat. No. 2,880,142, incorporated herein by reference, to subject the soil samples to the action of an organic liquid normally toxic to microorganisms, such as an alcohol, as the sole carbon and energy source for culturing the microorganisms. This method involved a direct measurement, or plate count, method (as opposed to the gas utilization methods discussed above wherein soil dilutions were placed on agar containing the alcohol and colonies were counted after a six-day incubation period. In this way, only those microorganisms which were not killed by the organic liquid and were able to utilize such organic liquid as a nutrient were counted. Thus, only the hydrocarbon-consuming microorganisms which have been consuming hydrocarbons attributable to petroleum deposits were those counted in this method. While this method offers the advantage of selectivity relative to other methods, it nonetheless has the disadvantages of the length of time required before results are available and of the laborious and time-consuming nature of counting colonies on an agar plate. Investigations subsequent to the issuance of U.S. Pat. No. 2,880,142 have revealed that not all of the microorganisms which are resistant to the organic compound and which grow on the agar plates are actually subsisting on such organic compound. To the contrary, a high proportion of such microorganisms are actually able to grow on the agar without any additional carbon source. Thus, the results obtained still may not accurately represent the number of hydrocarbon-consuming microorganisms present in the soil at the time of sampling.

In addition to the gas utilization and direct measurement, e.g., plate counting methods, the population of hydrocarbon-consuming microorganisms in a soil sample may be determined indirectly by measurements of the metabolic products of the hydrocarbon-consuming microorganisms. U.S. Pat. No. 2,269,889 to Blau, incorporated herein by reference, discloses a method which measures the bacterial oxidation products of the hydrocarbon gases. More specifically, it was believed that hydrocarbon-consuming bacteria in the soil polymerize the hydrocarbons derived from petroleum to form carboxylic acids. Thus, a chemical reagent such as sodium peroxide was employed to cause a color change by acting on the products of the microbial attack of the gases. It was further deemed possible to determine the presence of heavy organic bodies, resulting from the action of bacteria on the hydrocarbons, by examining soil samples with ultraviolet light. Oxidation-reduction potential measurements have also been found to be affected by the presence of oil deposits, presumably due to the action of bacteria on hydrocarbons. A number of shortcomings are associated with known techniques for assaying the metabolic products of hydrocarbon-consuming bacteria. Thus, as stated in U.S. Pat. No. 2,269,889, where such products are detected by a sodium peroxide-induced color change, the data collected are greatly affected by seasonal changes, the presence of calcium and magnesium in the soil, and the occurrence of any recent disturbances to the soil at the place from which the sample was taken.

From the above, it is apparent that none of the known techniques for determining the presence of hydrocarbon-consuming bacteria in a soil sample has met with great deal of success. Problems with false readings, too much subjectivity in the readings, unreasonably long time periods to complete the tests, and complexity of the analyzing techniques have pervaded this field. Not surprisingly, therefore, such techniques have gained only limited commercial acceptance.

SUMMARY OF THE INVENTION

In view of the foregoing limitations and shortcomings of prior art methods for microbiological prospecting, as well as other disadvantages not specifically mentioned above, it is apparent that there exists a need in the art for a method of microbiological prospecting for oil and gas which eliminates the above disadvantages which have limited the practical applicability of such prospecting in the past. It is, therefore, a primary objective of the present invention to fulfill that need with a method and system for microbiological prospecting for oil and gas which accurately detects the presence of hydrocarbon-consuming microorganisms. The process of this invention detects the enzymes employed by said microorganisms to metabolize the hydrocarbon nutrients into their more oxidized forms and provides an accurate means for the desired detection.

It is a further object of the present invention to provide a method and system for the microbiological prospecting for oil and gas which requires only relatively short periods of time to complete, such as between 24 and 72 hours.

Another object of the present invention is to provide a process for the microbiological prospecting for oil and gas which is performed in a liquid medium, thereby eliminating the need for agar, a potentially extraneous carbon source capable of supporting microorganisms other than the hydrocarbon-consuming microorganisms of interest, and eliminating the need for plate counting.

Another object of the present invention is to provide a process for the microbiological prospecting for oil and gas which is automatable, especially by computer controlled and monitored means.

In one aspect, the present invention comprises a method for the microbiological prospecting for oil and gas comprising the steps of:
(i) suspending a soil sample in a mineral salt solution;
(ii) adding to a gas-tight tube:
  (a) said suspended soil sample:
  (b) an additional portion of said mineral salt solution;
  (c) a selective growth substrate capable of providing electron-donating potential for hydrocarbon-consuming microorganisms, and
  (d) an oxidation-reduction dye capable of indicating by a change in color a change in the redox potential caused by the metabolism of hydrocarbon-consuming microorganisms;
(iii) sealing the tube and incubating the contents of the sealed tube to allow growth of hydrocarbon-consuming microorganisms present therein; and
(iv) observing any color change, or lack of color change, in the tube contents to determine the presence or absence of hydrocarbon-consuming microorganisms in the soil sample.

In another aspect, the present invention comprises a system for detecting the presence of hydrocarbon-consuming microorganisms in a soil sample comprising:
(i) a gas-tight tube having resealable opening means for introducing a soil sample into the tube; and,
(ii) sealed within said tube:
  (a) a soil sample suspended in a mineral salt solution;
  (b) a selective growth substrate capable of providing electron-donating potential for hydrocarbon-consuming microorganisms; and
  (c) an oxidation-reduction dye capable of indicating by a change in color a change in the redox potential caused by the metabolism of hydro-carbon-consuming microorganisms in the tube.

In another aspect, the present invention comprises a kit for detecting the presence of hydrocarbon-consuming microorganisms in a soil sample comprising:
(i) a gas-tight tube having resealable means for introducing a soil sample into the tube;
(ii) a mineral salt solution suitable for suspending a soil sample;
(iii) a selective growth substrate capable of providing electron-donating potential for hydrocarbon-consuming microorganisms; and
(iv) an oxidation-reduction dye capable of indicating by a change in color a change in electron redox potential caused by the metabolism of hydro-carbon-consuming microorganisms.

From the objects, advantages and features of the present invention apparent from the above and that will become apparent hereinafter, the nature and scope of the present invention may be more clearly understood by reference to the following detailed description of preferred embodiments and reference to the appended claims.

BRIEF DESCRIPTION OF THE DRAWINGS

FIG. 8 is a plot of the moving average of change in absorbance, $\Delta A$, for the soil samples from Survey No. 93 used in Example IV.

DETAILED DESCRIPTION OF PREFERRED EMBODIMENTS

Figure 1:
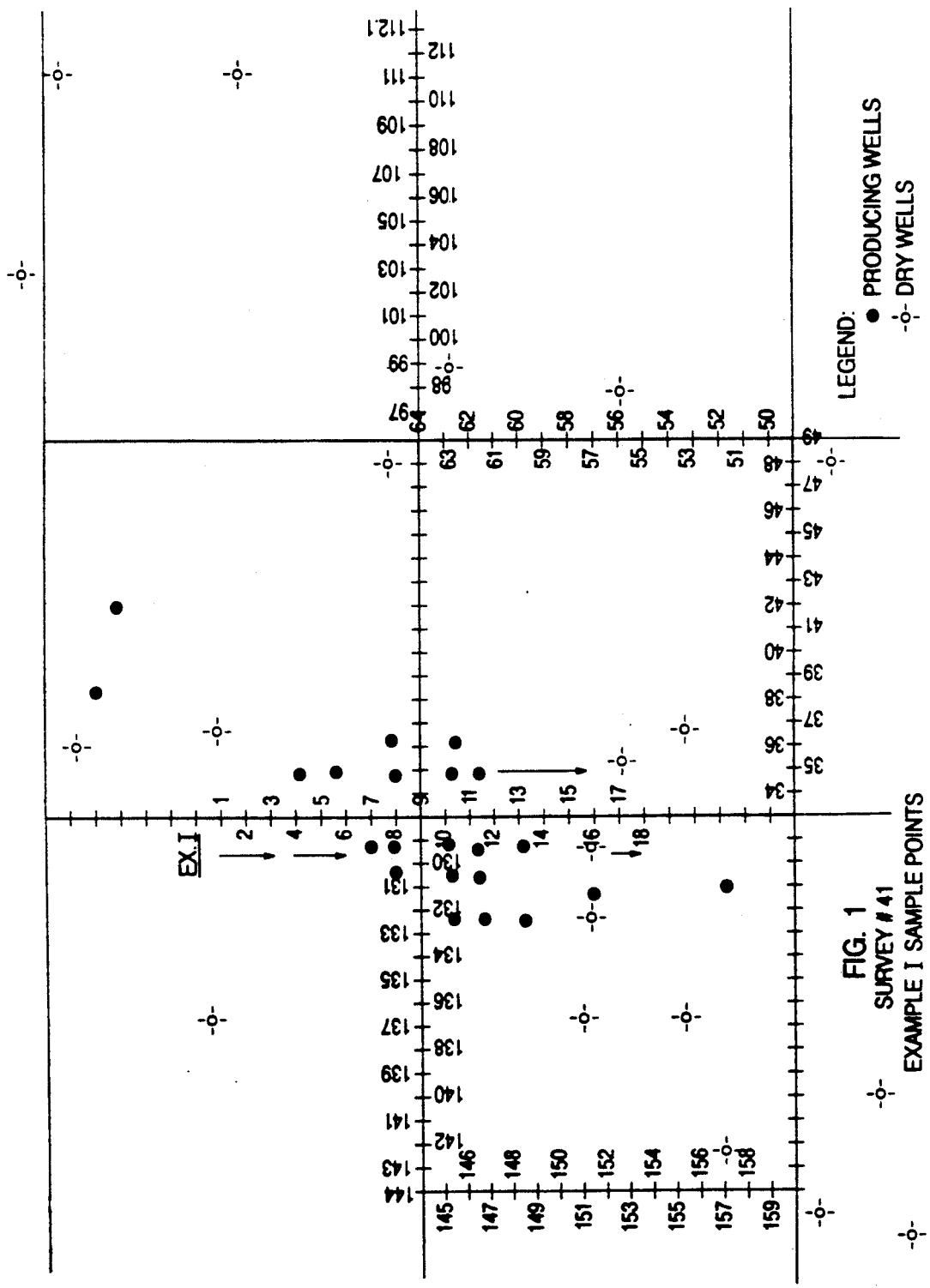
FIG. 1 is a plot of soil sample points on Survey No. 41 used in Example I.

The present invention enables detection of the presence of hydrocarbon-consuming microorganisms, and thus the determination of the presence of subterranean oil or gas deposits, through the detection of the enzymes employed by the hydrocarbon-consuming microorganisms to metabolize the hydrocarbons. More specifically, all organisms posses metabolic pathways responsible for their nutritional and growth characteristics. Such metabolic pathways require various enzymes which catalyze the molecular reactions necessary for the utilization of nutrients. In the case of hydrocarbon-consuming microorganisms, the metabolic pathway for oxidation degradation of aliphatic hydrocarbons is now known to proceed as follows:

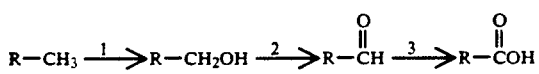

The enzyme catalyzing (1) the oxidation of the aliphatic hydrocarbon into an alcohol is mono-oxygenase. The enzyme catalyzing (2) the further oxidation of the alcohol to an aldehyde is alcohol dehydrogenase. Finally, the enzyme catalyzing (3) the oxidation of the aldehyde into a carboxylic acid is aldehyde dehydrogenase.

All of the above-mentioned enzymes belong to the more general class of enzymes known as oxido-reductase due to the fact that the reactions (1)–(3) above which they catalyze involve the transfer of electrons from an electron-donating substrate to an electron-accepting molecule. Thus, detection of these enzymes in a system containing only hydrocarbons or intermediates in their metabolism, i.e., the corresponding alcohol or aldehyde, as the nutrient provides an effective means for determining the presence of hydrocarbon-consuming microorganisms in a soil sample. Additionally, it will be recalled that one of the problems characterizing prior art approaches to detecting the presence of hydrocarbon-consuming microorganisms was the possibility of obtaining false positive readings since many non-hydrocarbon-consuming microorganisms are able to grow on the non-hydrocarbon nutrients present in agar plates. The present invention avoids such false positive readings since only hydrocarbon-consuming microorganisms present in a sample will be detected in accordance with the method of the present invention.

The assay method of the present invention is carried out by suspending a soil sample in a liquid medium and more particularly, in a mineral salt solution. In the prior art method, assay techniques were carried out on agar plates rather than in a liquid medium, but it was found that despite the use of substances toxic to most microorganisms except the hydrocarbon-consuming ones as the sole nutrient, erroneous readings were nonetheless a problem since some non-hydrocarbon-consuming microorganisms were able to utilize the agar itself as a nutrient. As a result, colony counts on the plate were frequently inaccurately high.

The mineral salt solutions which may be employed according to the present invention are those solutions well known in the ar for cultivating microorganisms. Exemplary mineral salt solutions are as follows:

| Component | Weight (g) |
|---|---|
| $NH_4NO_3$ | 1.0 |
| $MgSO_4.7H_2O$ | 0.1 |
| $K_2HPO_4$ | 0.5 |
| $CaSO_4$ | 0.012 |
| Distilled Water | 1000 |
| $(NH_4)_2SO_4$ | 2.00 |
| $K_2HPO_4$ | 0.30 |
| $Na_2HPO_4$ | 0.20 |
| $MgSO_4\ 7H_2O$ | 0.10 |
| $CaCl_2$ | 0.01 |
| Distilled Water | 1000 |

The above solutions are presented merely for purposes of illustration. One skilled in the art will appreciate that the specific mineral salts selected are not important so long as they fulfill the basic and well known mineral requirements of the microorganisms for which the soil samples are being tested. For example, $NH_4Cl$ may be substituted for $NH_4NO_3$, $MgNH_4PO_4$ may be substituted for $MgSO_4$, etc., as is conventionally done for culturing various microorganisms. The pH of the mineral salt solution will preferably be about 7.0 but may vary slightly, such as from about 6.8 to about 7.2, provided the higher or lower pH is not incompatible with growth conditions for the hydrocarbon-consuming microorganisms.

After suspending the soil sample in the mineral salt solution, the suspended sample is combined with a selective growth substrate capable of acting as a selective electron-donating growth substrate for hydrocarbon-consuming microorganisms and with an oxidation-reduction dye capable of indicating a change in the redox potential of the solution caused by the enzyme activities and metabolic products formed by the growth of hydrocarbon-consuming microorganisms.

The selective growth substrate is chosen to provide readily metabolizable source of carbon. Preferred selective growth substrates are alcohols or aldehydes. Other growth substrates, such as the hydrocarbon gases, can be used provided that they are selective to hydrocarbon-consuming microorganisms, i.e., do not promote growth of other microorganisms which may be present in the soil samples. The growth substrate must also be compatible with the mineral salt solution and the dye used in this invention. The alcohols and aldehydes are preferably those having the same carbon chain length as the gases released from the subterranean oil deposits and frequently found in the soil. Since these gases usually contain from one to about four carbon atoms, the aliphatic alcohols are suitable, such as methanol, ethanol, 1-propanol, 2-propen-1-ol, 1-butanol, 2-butanol, 2-methyl-2-propanol, 2-buten-1-ol, 3-buten-1-ol, and 3-buten-2-ol. Particularly preferred are the normal aliphatic alcohols such as methanol, ethanol, 1-propanol, and 1-butanol. Similarly, suitable aldehydes are aliphatic and have from one to about four carbon atoms and correspond to the above-mentioned alcohols.

Since the culture medium is devoid of any sources of carbon other than the above-described alcohols or aldehydes, and since the hydrocarbon-consuming microorganisms are among the very few which can survive, much less metabolize the alcohol or aldehyde substrate, the chances of false positive readings is further reduced.

As previously indicated, the presence of the oxido-reductases indicative of hydrocarbon-consuming microorganisms is determined through the use of an oxidation-reduction dye or combinations of such dyes capable of accepting electrons from enzymes involved in hydrocarbon metabolism and thus produced by hydrocarbon-consuming microorganisms. When actual electron transfer is not involved, the dye detects and responds to the change in the redox potential. Exemplary of such dyes are resazurin, methylene blue, the tetrazolium dyes such as triphenyl tetrazolium chloride and the combination of N-methyl-phenazinium methosulfate, dichlorophenol indophenol. A preferred dye is resazurin. It will be appreciated, however, that other dyes of similar or different oxidation-reduction potentials may be employed in the present invention, although appropriate adjustments in the test conditions will have to be made according to the properties of the dye selected. Additional dyes are disclosed in the CRC Handbook of Biochemistry, 2ndth Edition, 19 . "Oxidation-Reduction Potentials Absorbance Bonds and Molar Absorbance of Compounds Used in Biochemical Studies" at pages J-36 through J-39, and the selection and use of dyes in the present invention involves many of the same criteria commonly applied in selecting oxidation-reduction dye indicators for oxidoreductase reactions.

The methods of taking a soil sample for determining the presence of hydrocarbon-consuming microorganisms therein are generally as described in the art. The samples are taken at depths between about 4 and about 12 inches. The precise depth at which the soil is taken depends on soil conditions, e.g., rock content, previous cultivation of the soil, and the like. The depth should be great enough such that undisturbed soil is sampled, but not so great such that sampling expediency is hindered. The preferred sample depth is 6 to 10 inches. Samples may be taken over a field of interest according to patterns well known to persons skilled in the art.

The sample is then combined with the sterile mineral salt solution. In general, a 5 to 50 g soil sample should be combined with 20 to 200 ml of the mineral solution. The minimum amount of soil will be determined by the amount of soil sample available and having sufficient concentration of n the solution for effective indication by the dyeing sufficient solution present for a given amount f soil sample to provide a sufficiently dispersed suspension of the soil to allow intimate mixing of the soil sample with the selective growth substrate and dye. A preferred ratio is 25 g of soil with 100 ml of mineral salt solution.

After the soil sample and the mineral salt solution have been combined, they are mixed to form a suspension of the soil in the mineral salt solution. In general, such a suspension may be prepared by simply shaking the mixture normally by hand or using an automatic shaker or vortex mixer for a period of about 1 minute. The suspension may also be prepared using a blender, but it is preferred to prepare the suspension in each individual gas-tight tube or preferably other appropriate container by manual or machine shaking to maintain sterility and avoid cross-contamination between samples.

After mixing, the soil suspension is generally subjected to a serial dilution with additional mineral salt solution to obtain a 10 to 1,000 fold dilution in the mineral salt solution. Then 1 ml of the diluted suspension is combined in a sterile, gas-tight glass tube with an appropriate amount of mineral solution to which the desired concentration of redox dye has been added. Preferably, a 100 fold dilution of the soil suspension is prepared and 1 ml of the diluted suspension is added to 4 ml of the redox dye solution in the glass tube. The amount of redox dye added is determined by its extinction coefficient. In general, the concentration of the dye should be such that an absorbance reading of approximately one is achieved in the tube.

The selective growth substrate, preferably an alcohol, is then added to the tube containing the dilute soil suspension and redox dye. The amount of alcohol added should be enough so as to be toxic to microorganisms not possessing the pathway for hydrocarbon utilization and enough to support growth of hydrocarbon-consuming microorganisms. This varies for each type of alcohol used, but usually enough alcohol should be added to result in a solution in the gas-tight tube containing between about 0.05% and 0.5% and preferably between about 0.1% and 0.2% by volume of the alcohol.

The tubes are capped with teflon-lined screw caps, vortexed and incubated at a temperature and for a period of time sufficient for the micro-organisms to grow and produce enzymes to react with the dye. Generally, incubation temperatures ranging between about 30° and about 40° C. and a period of about 48 to about 96 hours are sufficient. A preferred incubation is at about 35° C. for about 48 to about 72 hours. The extent of the reduction of the dye and thus, the amounts of oxido-reductase present, may be measured by observing the decrease in absorbance of the oxidized form of the dye—at a wave length where it exhibits an absorption peak—using a spectrophotometer. For example, the peak absorption for oxidized resazurin is at 598 nm. Other dyes have their own characteristic absorption peaks and molar extinction coefficient (defined as the absorbance of a 1 molar solution of the substance with a light path of 1 cm) which can be used by one skilled in the art to select an appropriate dye for the tests to be designed and carried out according to the present invention. The difference between the initial reading and the final reading indicates the extent of the reduction of the dye.

In the practice of this invention, the samples yielding the largest changes in the absorbance are those which contain the greatest amounts of the oxido-reductase enzymes and thereby indicating the presence of the greatest numbers of the hydrocarbon-consuming microorganisms indicative of the presence of subterranean oil or gas deposits.

The tubes used in the practice of this invention must be sterile and have resealable opening means for introducing the soil sample, selective growth substrate, mineral salt solution and dye. It is important that the tube be sealed gas-tight to avoid contamination from outside the tube and to prevent oxygen from entering the tube during the incubation period. It is essential for the function of the redox dye in this invention that the tubes be sealed gas-tight. The tubes are preferably glass, but may be made of other materials, so that the color change of the sample in the tube can be observed and measured without opening the tube. The tube material should not interfere with the light wave lengths measured, which is preferably by a spectrophotometer.

It can be seen that the practice of the present invention is readily adaptable to kits of tubes for easy field use and preparation, as well as automated, computerized testing system for preparation, incubation and color change measurements of the test samples. The kits can comprise gas-tight, sterile tubes adapted for receiving measured and prepared soil samples in the field. Preferably the kits will comprise initial sets of sterile containers for the collection and the initial preparation, suspension and dilution of the soil samples, and a set of gas-tight, sterile tubes for the final test sample to be combined with the selective growth substrate and dye. In a preferred system, the final test samples are prepared and placed in the gas-tight tubes in the field. The sealed tubes are incubated and the color changes read spectrophotometrically. In a similar preferred system, the soil samples are collected and sent to the laboratory in individual sterile containers where the entire operation can be carried out by automatic equipment, including the suspension and dilution aspect of sample preparation.

The following example is given by way of illustration and should not be interpreted as limiting the scope of the subject matter disclosed and claimed.

EXAMPLES

In each of the following examples, soil samples were collected 100 yards apart in a straight line going across a known producing oil field. Twenty-five grams of each soil sample were suspended in 100 ml of sterile mineral medium at pH 7.2 and having the following composition.

| | |
|---|---|
| $NH_4NO_3$ | 1.0 gram |
| $MgSO_4.7H_2O$ | 0.1 gram |
| $K_2HPO_4$ | 0.5 gram |
| $CaSO_4$ | 0.012 gram |
| Deionized water | 1 liter |

The soil suspension was agitated for approximately one minute and a 1:100 dilution was made in the mineral medium. A 1.0 ml aliquot of the 1:100 dilution was transferred to a 13 mm by 100 mm teflon-lined screw cap tube containing 4 ml of said mineral medium to which butanol was added to a final concentration of 0.2%, a redox dye, resazurin was added to a final concentration of 5 mg/l. The tubes were vortexed and incubated at 35° C. for 48 hours. The extent of reduction of the dye was measured by the decrease in absorbance at 598 nm of the oxidized molecule with a spectrophotometer. The difference between the initial (prior to addition of the second soil suspension) and final absorbance readings at this wavelength gives a measure of the extent of reduction of the dye.

EXAMPLE I

Figure 2:
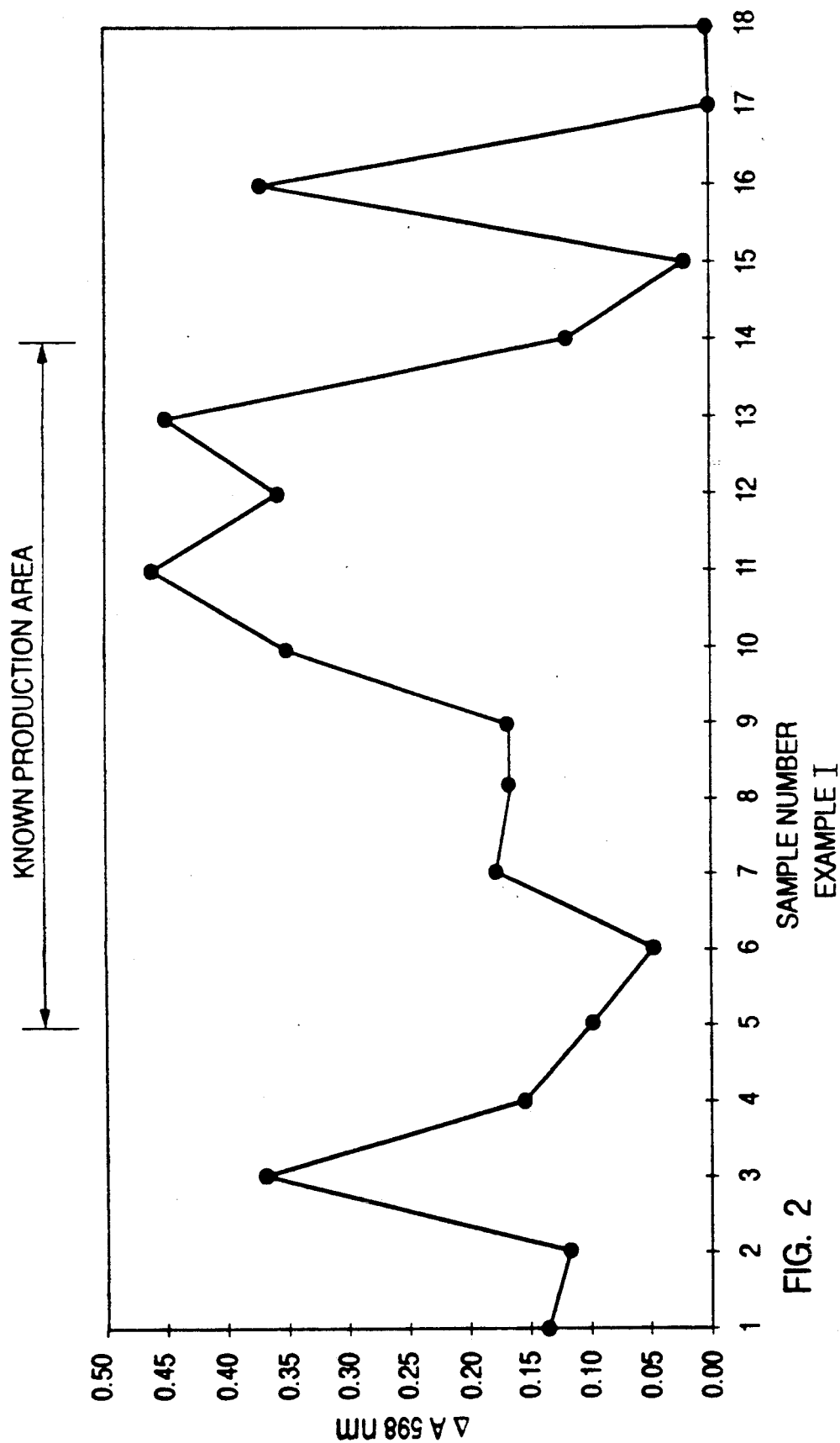
FIG. 2 is a plot of the raw data of the change in absorbance, $\Delta A$, for the soil samples from Survey No. 41 used in Example I and shown in Table I.

The soil samples for Example I were taken from Survey No. 41 at the locations shown in FIG. 1 for sample points 1 through 18. The soil samples from Survey No. 41 were tested as outlined above, except that the incubation period was 65 hours. The change in absorbance, $\Delta A$, was measured for each sample at 598 nm. The measurements for each sample are shown below in Table I and plotted in FIG. 2. In the following table, the "moving average" has been computed in accordance with the disclosure at Column 8 of U.S. Pat. No. 2,665,237 to Strawinski, the disclosure of which is incorporated herein by reference. This moving average is plotted in FIG. 3.

TABLE I

Figure 3:
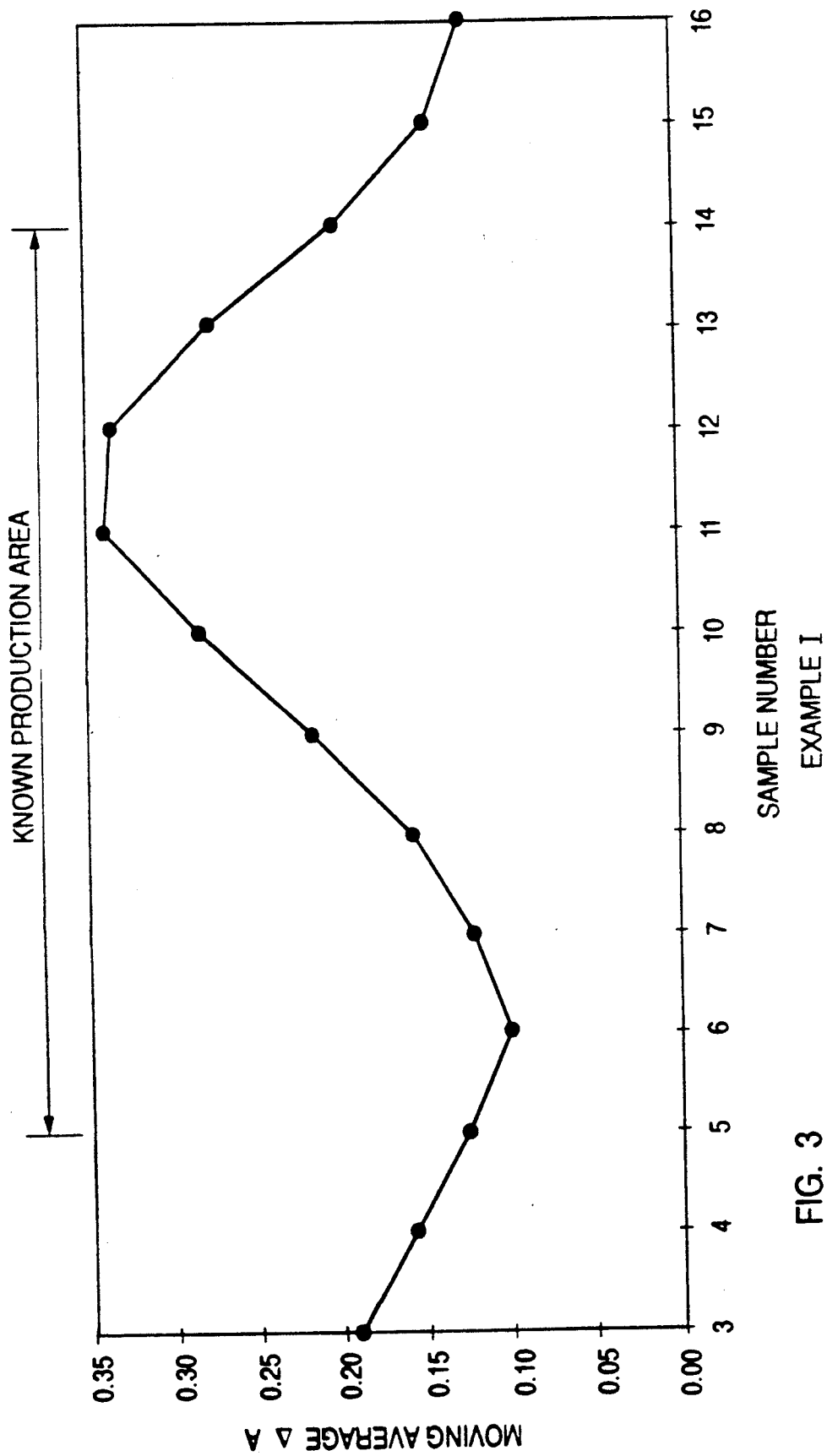
FIG. 3 is a plot of the moving average of the change in absorbance, $\Delta A$, computed from the data in Table I.

| Sample # | $\Delta A$ | 3-Sample Total | FIG. 3 Moving Average |
|---|---|---|---|
| 1 | 0.14 | | |
| 2 | 0.12 | 0.63 | |
| 3 | 0.37 | 0.65 | 0.19 |

TABLE I-continued

| Sample # | $\Delta A$ | 3-Sample Total | FIG. 3 Moving Average |
|---|---|---|---|
| 4 | 0.16 | 0.63 | 0.16 |
| 5 | 0.10 | 0.31 | 0.13 |
| 6 | 0.05 | 0.33 | 0.10 |
| 7 | 0.18 | 0.40 | 0.13 |
| 8 | 0.17 | 0.52 | 0.16 |
| 9 | 0.17 | 0.69 | 0.22 |
| 10 | 0.35 | 0.98 | 0.28 |
| 11 | 0.46 | 1.17 | 0.34 |
| 12 | 0.36 | 1.27 | 0.34 |
| 13 | 0.45 | 0.93 | 0.28 |
| 14 | 0.12 | 0.59 | 0.20 |
| 15 | 0.02 | 0.51 | 0.15 |
| 16 | 0.37 | 0.39 | 0.13 |
| 17 | 0.00 | 0.37 | |
| 18 | 0.00 | | |

As can be seen from FIG. 3 and FIG. 1, the correlation of the moving average of $\Delta A$ correlates well with the known producing area.

EXAMPLE II

Figure 4:
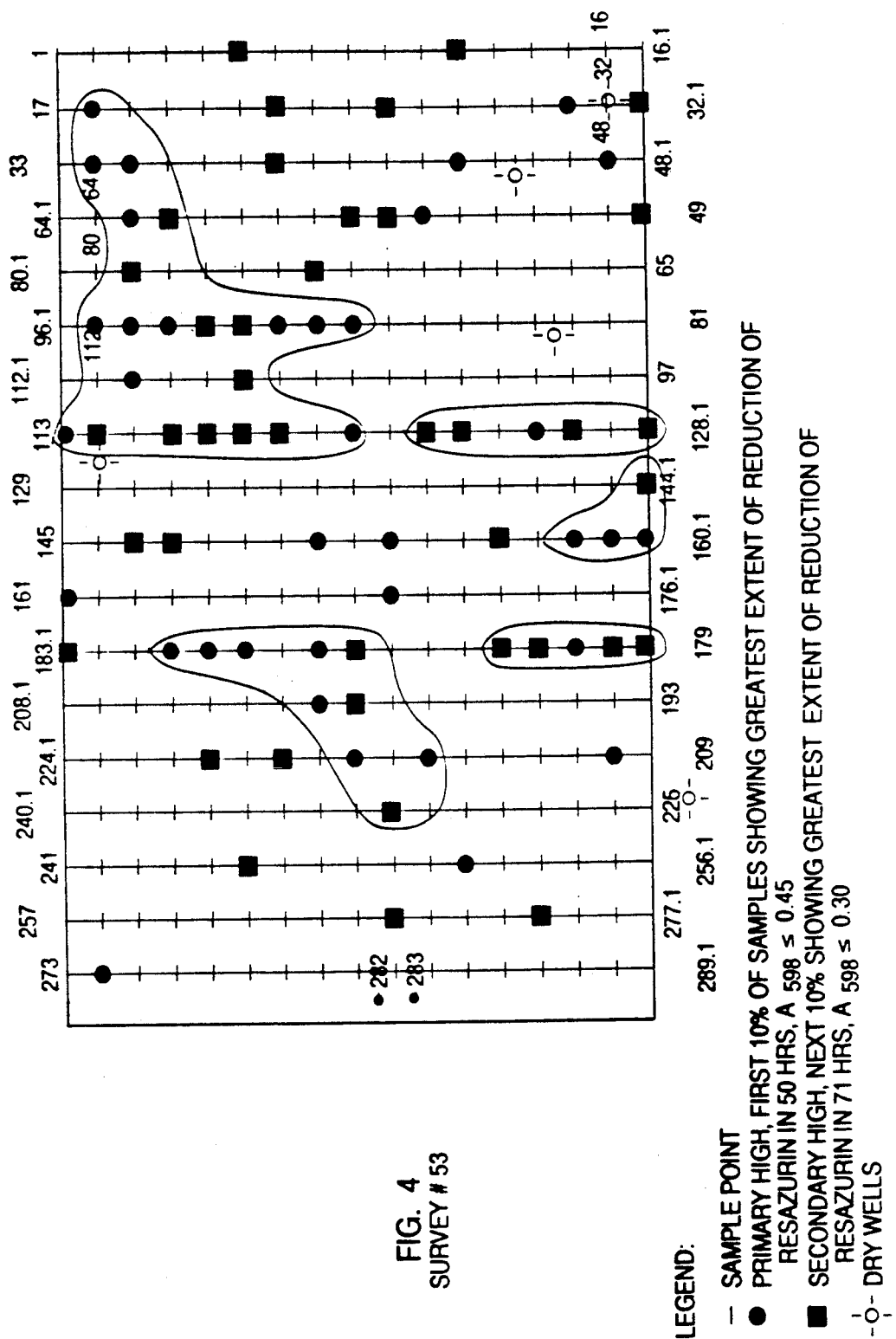
FIG. 4 is a plot of Survey No. 53 showing the sample points for the soil samples used in Example II and showing the primary high and secondary high sample points.

In this example, samples were taken from Survey No. 53 and the same assaying method was followed as described above and in Example I. However, instead of computing and plotting the moving average of the change of absorbance values based on a single reading at 65 hours, in this example, the $\Delta A$ readings were taken at 50 and 71 hours. The "primary high" represented by the round dots on FIG. 4 are the 10% of the samples that show the greatest reduction of the dye in 50 hours, and the "secondary high" represented by the square dots on FIG. 4 are the next 10% showing the greatest reduction in the dye in 71 hours. The contour lines in FIG. 4 delineate the areas of highest probability of oil deposits. This example from Survey No. 53 did not cross any known production areas. Nevertheless, the lack of positives in the plots shown in FIG. 4 correlate well with the known dry wells in the are indicating that the present invention does not give false positive indications.

EXAMPLE III

Figure 5:
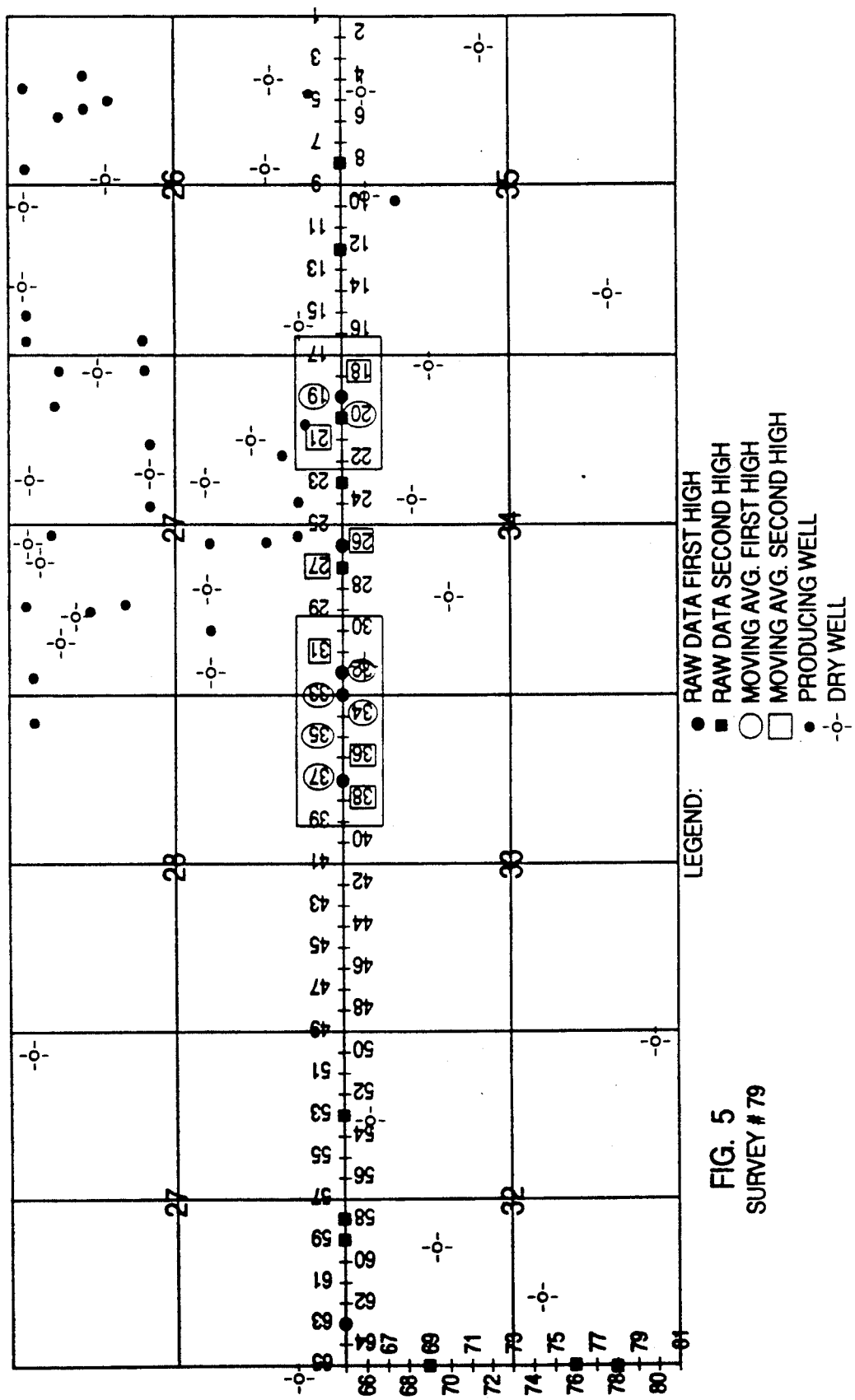
FIG. 5 is a plot of Survey No. 79 showing the soil samples used in Example III.

In this example, samples were taken from Survey No. 79 and processed as described above. The assaying method was the same, except the $\Delta A$ readings were taken in 48 hours. In FIG. 5 the round dots on the data points show the sample points for the top 10% of the samples showing dye reduction, while the square dots show the sample points for the second 10% of the samples. Also in FIG. 5, the moving average for the first 10% are shown in the round circles and the moving average for the second 10% are shown in the square boxes.

Figure 6:
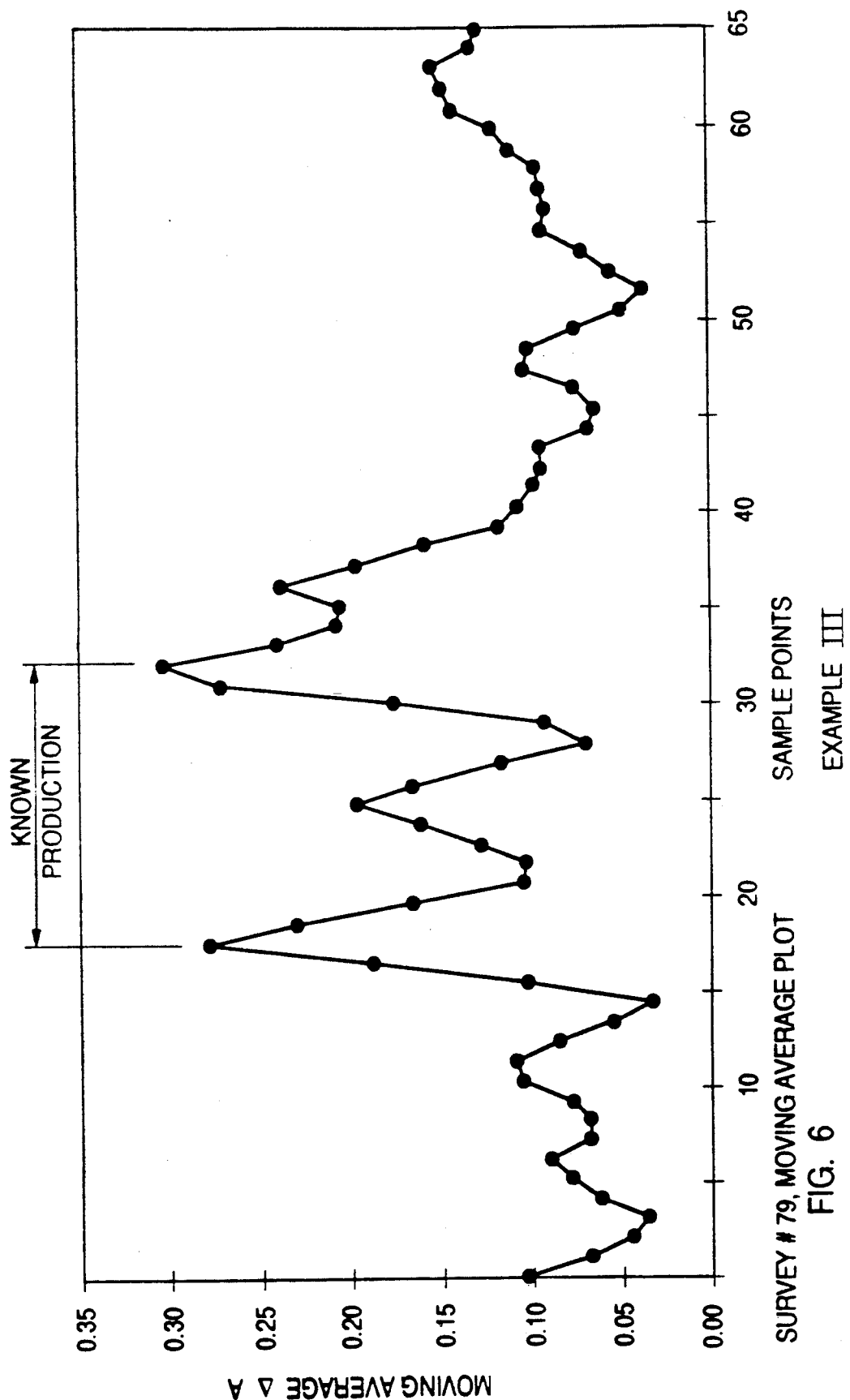
FIG. 6 is a plot of Survey No. 79 showing the moving average of change in absorbance, $\Delta A$, for the soil samples from Survey No. 79 used in Example III.

FIG. 6 shows a plot of the moving average of $\Delta A$ for Survey No. 79 and shows a good correlation between the moving average $\Delta A$ and the known production area.

EXAMPLE IV

Figure 7:
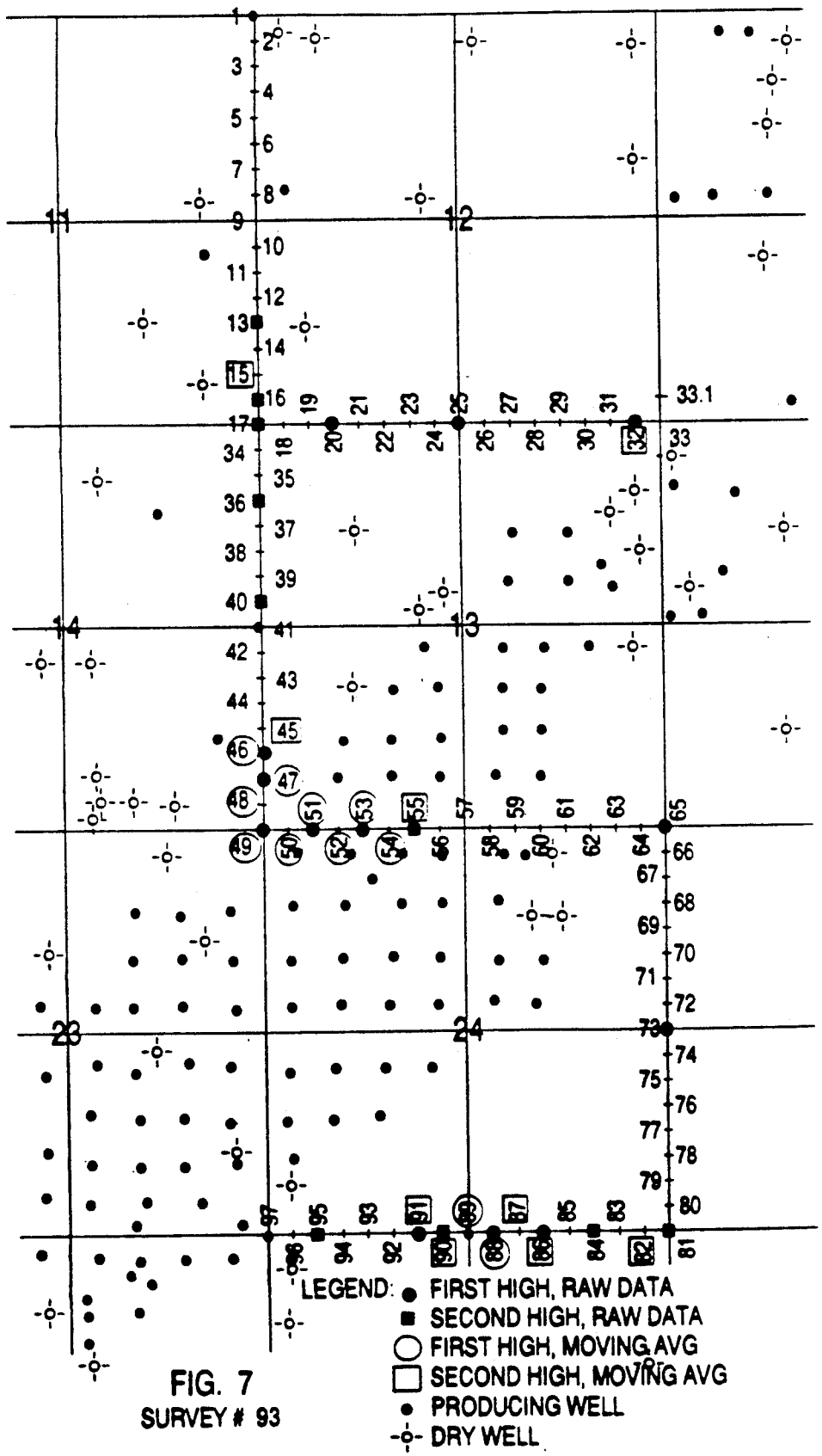
FIG. 7 is a plot of Survey No. 93 showing the sample points of the soil samples used in Example IV.

In this example, samples were taken as shown in FIG. 7 in Survey No. 93 and the samples were processed and evaluated the same as in Example III. On the Survey No. 93 plot in FIG. 7, the round dots indicate the first high in $\Delta A$, the square dots indicate the second high in $\Delta A$, the round circles indicate the first high of the moving average and the square boxes indicate those sample points constituting the second high in the moving average of ΔA. FIG. 8 shows a plot of the moving average of ΔA for the samples in this example. As in the above examples, the correlation between the moving average ΔA and the known production area is good.

Although only preferred embodiments are specifically described herein, it will be appreciated that many modifications and variations of the present invention are possible in light of the above teachings and within the purview of the claims without departing from the spirit and intended scope of the invention.

What is claimed is:

1. Method for microbiological prospecting for oil or gas comprising the steps of:
    (i) suspending a soil sample in a mineral salt solution;
    (ii) adding to a gas-tight tube;
        (a) said suspended soil sample,
        (b) an additional portion of said mineral salt solution,
        (c) a selective electron-donating growth substrate capable of providing electron-donating potential for a hydrocarbon-consuming microorganism; and
        (d) an oxidation-reduction dye capable of indicating by a change in color a change in the redox potential caused by growth of a hydrocarbon-consuming microorganism;
    (iii) sealing the tube and incubating the contents of the sealed tube to allow growth of a hydrocarbon-consuming microorganism present therein; and
    (iv) observing color change in the tube contents to determine the presence of a hydrocarbon-consuming microorganism in said soil sample.

2. A method according to claim 1 wherein the selective growth substrate comprises an alcohol or an aldehyde.

3. A method according to claim 1 wherein the dye comprises resazurin, methylene blue, or a tetrazolium dye.

4. A method according to claim 2 wherein the dye comprises resazurin, methylene blue, or a tetrazolium dye.

5. A method according to claim 1 wherein the color change is measured by spectrophotometric means and an automatable means compares the color change to predetermined color standards and calculates a quantitative indication of the presence of a hydrocarbon-consuming microorganism in the soil sample.

6. A system for detecting the presence of a hydrocarbon-consuming microorganism in a soil sample comprising:
    (i) a gas-tight tube having resealable means for introducing a soil sample into the tube;
    (ii) sealed within said tube:
        (a) a mineral salt solution;
        (b) a selective growth substrate capable of providing electron-donating potential to a hydrocarbon-consuming microorganism; and
        (c) an oxidation-reduction dye capable of indicating by a change in color a change in the redox potential caused by growth of a hydracarbon-consuming microorganism in the tube.

7. A system according to claim 6 wherein a soil sample is dispersed in the mineral salt solution.

8. A system according to claim 6 wherein the selective growth substrate comprises an alcohol or an aldehyde.

9. A system according to claim 7 wherein the selective growth substrate comprises an alcohol or an aldehyde.

10. A system according to claim 8 wherein the dye comprises resazurin, methylene blue, or a tetrazolium dye. the dye comprises resazurin, methylene blue, or a tetrazolium dye 11. A system according to claim 9 wherein the dye comprises resazurin, methylene blue, or a tetrazolium dye.

12. A system according to claim 10 wherein the system further comprises spectrophotometric means for measuring a color change in the dye and automatable means for comparing the color change to a predetermined standard and calculating a quantitative indication of the presence of a hydrocarbon-consuming microorganism in the soil sample.

13. A system according to claim 11 wherein the system further comprises spectrophotometric means for measuring a color change in the dye and automa-table means for comparing the color change to a predetermined standard and calculating a quantitative indication of the presence of a hydrocarbon-consuming microorganism in the soil sample.

14. A kit for detecting the presence of hydrocarbon-consuming microorganisms in a soil sample comprising:
    (i) a gas-tight tube having resealable opening means for introducing a soil sample into the tube; and,
    (ii) sealed within said tube:
        (a) a soil sample suspended in a mineral salt solution;
        (b) a selective growth substrate capable of providing electron-donating potential for hydrocarbon-consuming microorganisms; and
        (c) an oxidation-reduction dye capable of indicating by a change in color a change in the redox potential caused by growth of a hydrocarbon-consuming microorganism in the tube.

15. A kit according to claim 14 wherein the selective growth substrate comprises an alcohol or an aldehyde.

16. A kit according to claim 14 wherein the dye comprises resazurin, methylene blue, or a tetrazolium dye 17. A kit according to claim 15 wherein the dye comprises resazurin, methylene blue, or a tetrazolium dye.

* * * * *

UNITED STATES PATENT AND TRADEMARK OFFICE
CERTIFICATE OF CORRECTION

PATENT NO. : 5,093,236                  Page 1 of 2

DATED : March 3, 1992

INVENTOR(S) : Gonzales-Prevatt, et al.

It is certified that error appears in the above-identified patent and that said Letters Patent is hereby corrected as shown below:

On the title page at item [63] the filing date of the parent application "September 14, 1989" should read --September 14, 1988--.

In Column 1, line 45 "wa" should be --was--.

In Column 2, line 24 "above" should appear as --above)--.

In Column 5, line 67 "ar" should be --art--.

In Column 7, line 17 "2ndth Edition, 19 ." should read --2nd Edition, 1970--; lines 42-44, delete "n the solution for effective indication by the dyeing sufficient solution present for a given amount f", and insert therefor --potential hydrocarbon-consuming microorganism present in the solution for effective indication by the days. The upper limit is determined by convenience and by having sufficient solution present for a given amount of --.

UNITED STATES PATENT AND TRADEMARK OFFICE
CERTIFICATE OF CORRECTION

PATENT NO.  : 5,093,236
DATED       : March 3, 1992
INVENTOR(S) : Gonzales-Prevatt, et al It is certified that error appears in the above-indentified patent and that said Letters Patent is hereby corrected as shown below:

In Column 10, line 40, "are" should read -- area--.

Signed and Sealed this

Seventh Day of December, 1993

Attest:

BRUCE LEHMAN

Attesting Officer       Commissioner of Patents and Trademarks